United States Patent [19]

Engels et al.

[11] Patent Number: 5,659,025
[45] Date of Patent: Aug. 19, 1997

[54] 3'-(2')-AMINO OR THIOL-MODIFIED, FLUORESCENT DYE-COUPLED OLIGONUCLEOTIDES AND A PROCESS FOR THE PREPARATION AND THE USE THEREOF

[75] Inventors: Joachim Engels, Kronberg/Taunus; Mathias Herrlein, Frankfurt am Main; Renate Konrad, Sulzbach/Taunus; Matthias Mag, Oberursel, all of Germany

[73] Assignee: Hoechst Aktiengesellschaft, Frankfurt am Main, Germany

[21] Appl. No.: 457,377

[22] Filed: Jun. 1, 1995

Related U.S. Application Data

[62] Division of Ser. No. 184,759, Jan. 18, 1994, which is a continuation of Ser. No. 803,953, Dec. 9, 1991, abandoned.

[30] Foreign Application Priority Data

Dec. 11, 1990 [DE] Germany ............... 40 39 488.3

[51] Int. Cl.$^6$ ............................................. C07H 21/00
[52] U.S. Cl. .............. 536/23.1; 536/25.3; 536/25.32; 536/25.33; 536/25.34; 536/25.5; 435/6
[58] Field of Search ............... 536/23.1, 25.3, 536/25.33, 25.34, 25.5, 25.32; 435/6

[56] References Cited

U.S. PATENT DOCUMENTS

| | | |
|---|---|---|
| 4,849,513 | 7/1989 | Smith et al. . |
| 5,015,733 | 5/1991 | Smith et al. . |

FOREIGN PATENT DOCUMENTS

| | | |
|---|---|---|
| 2236852 | 4/1991 | United Kingdom . |
| WO 88/00201 | 1/1988 | WIPO . |

OTHER PUBLICATIONS

Sanger et al., Proc. Natl. Acad. Sci. USA, 74, 5463–5467 (1977).
Smith et al., Nature 321, 674–679 (1986).
Prober et al., Science, 238, 336–341 (1987).
Trainor, Anal. Chem., 62, 418–426 (1990).
Voss et al., Nucleic Acids Research, 17, 2517–2526 (1989).
Carrano et al., Genomics, 4, 129–136 (1989).
Brenner et al., Proc. Natl. Acad. Sci. USA, 86, 8902–8906 (1989).
Mungall et al., J. Org. Chem., 40, 1659–1662 (1975).
Mag et al., Nucleic Acids Research, 17, 5973–5989 (1989).
Smith et al., Nucleic Acids Research, 13, 2399–2413 (1985).
Hodges et al., Biochemistry, 28, 261–267 (1989).
Swerdlow et al., Nucleic Acids Research, 18, 1415–1419 (1990).
Cohen et al., Proc. Natl. Acad. Sci. USA, 85, 9660–9663 (1988).
Swerdlow et al., J. of Chromatography, 516, 61–67 (1990).
Efimov et al., Nucleic Acids Research, 11, 8369–8387 (1983).

*Primary Examiner*—James O. Wilson
*Attorney, Agent, or Firm*—Finnegan, Henderson, Farabow, Garrett & Dunner, L.L.P.

[57] ABSTRACT

The OH group located in the 3' and/or 2' position of a nucleoside, nucleotide or oligonucleotide is derivatized to an amino or thiol group and subsequently a fluorescent dye is coupled thereto. The resulting 3'- and/or 2'-amino- and thiol-modified nucleosides, nucleotides and oligonucleotides can then be used for the synthesis of complementary strands in the presence of a template strand or of oligonucleotides and for the detection of genetic material. They have the advantage that the fluorescent label need no longer be attached to the 5' end of the oligonucleotide or to the nucleobase, and thus need not be introduced during the chemical synthesis as in labeling techniques hitherto known, while the known and conventional methods have the disadvantage that only a few polymerases can be employed for the synthesis, the acceptance of the triphosphates by the polymerases diminishes and, moreover, a large substrate excess is necessary.

3 Claims, No Drawings

3'-(2')-AMINO OR THIOL-MODIFIED, FLUORESCENT DYE-COUPLED OLIGONUCLEOTIDES AND A PROCESS FOR THE PREPARATION AND THE USE THEREOF

This is a division of application Ser. No. 08/184,759, filed Jan. 18, 1994, pending, which is a continuation application of Ser. No. 07/803,953, filed Dec. 9, 1991, abandoned.

BACKGROUND OF THE INVENTION

1. Field of the Invention

3'-(2')-Amino- or thiol-modified, fluorescent dye-coupled nucleosides, nucleotides and oligonucleotides, and a process for the preparation and the use thereof

2. Description of the Related Art

Labeled oligonucleotides have found an extremely large number of uses in genetic engineering because they are easier to handle than the DNA probes which are conventionally used as hybridization probes and are prepared from native gene material by restriction digestion.

Labeled oligonucleotides which are employed in the form of so-called antisense DNA oligonucleotides are able to intervene in cellular events in a regulating manner and are thus becoming of increasing importance, for example for the in vivo investigation of protein expression. According to present knowledge, the mechanism takes place via DNA-DNA, DNA-RNA and RNA-RNA interactions but the details have not yet been elucidated.

Labeled oligonucleotides are used in vitro for example for the identification of gene fragments within a gene bank by using the labeled oligonucleotide to probe and identify blotted gene probes of the gene bank.

In order to be able to carry out such experiments in vitro or in vivo, the oligonucleotides must, as already mentioned, be labeled. Besides radioactive labeling by suitable isotopes, one form of non-radioactive labeling which has already been used is derivatized fluorescent dyes which offer the possibility of easier and less hazardous handling.

To date, a technique of this type has also already been used successfully for the non-radioactive sequencing of DNA. The approaches for this are essentially based on the method of Sanger (F. Sanger, S. Nicklen and S. Coulson, Proc. Natl. Acad. Sci. USA 74, 5463 (1977)).

The fluorescent label is attached (G. L. Trainor, Anal. Chem. 62, 418 (1990)) either at the 5' end of the oligonucleotide (L. E. Hood, L. M. Smith and C. Heiner, Nature 321, 674 (1986)) or at the nucleobase (J. M. Prober, G. L. Trainor and R. J. Dam, Science 238, 336 (1987)). A crucial disadvantage of the last-mentioned method derives from the fact that the fluorescent labeling is introduced during the synthesis, i.e. during the polymerization and, in this case, specifically during the enzymatic polymerization. This step in the method has the consequences that only a few polymerases can now be used for the synthesis, that the acceptance of the triphosphates by the polymerases is diminished and that, moreover, a large substrate excess is necessary.

However, the introduction of a fluorescent label is not confined to Sanger sequencing. Maxam-Gilbert chemical sequencing with a fluorescent label is also known (H. Voss, C. Schwager, U. Wirkner, B. Sproat, J. Zimmermann, A. Rosenthal, H. Erfle, J. Stegemann and W. Ansorge, Nucl. Acids Res. 17, 2517 (1989)).

In analogy to this, the mapping of restriction fragments with fluorescence detectors is also described (A. V. Carrano, J. Lamerdin, L. K. Ashworth, B. Watkins, E. Branscomb, T. Slezak, M. Raff, P. J. de Jong, D. Keith, L. McBride, S. Meister, M. Kronick, Genomics 4, 129 (1989) and S. Brenner and K. J. Livak, Proc. Natl. Acad. Sci. USA 86, 8902 (1989)).

SUMMARY OF THE INVENTION

It has now been found that a fluorescent dye can be coupled via an amino or thiol group in the 3'-(2') position (in α or β position) of a nucleoside, nucleotide or oligonucleotide, and this compound can advantageously be used to synthesize complementary strands in the presence of a template strand or of oligonucleotides, and to detect genetic material in vivo and in vitro.

The invention thus relates to:

1. A substance of the formula I

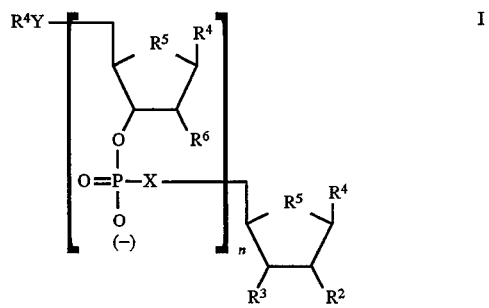

in which $R^1$ is a purine or pyrimidine base, at least one of the radicals $R^2$ and $R^3$ is a fluorescent dye in α or β position bonded via an amino or thiol group, and the other radical is optionally hydrogen, a hydroxyl, protected hydroxyl or methoxy group in α or β position, n is a number $\geq 0$, $R^4$ is a 5' protective group or phosphate, pyrophosphate, triphosphate, $R^5$ is oxygen, fluoromethylene, difluoromethylene or methylene, $R^6$ is a hydroxyl or methoxy group or hydrogen in α or β position, where $R^1$, $R^5$ and $R^6$ can in each case have identical or different meanings, Y and X are oxygen, sulfur, NH or methylene where X and Y can in each case be identical or different.

2. A process for the preparation of the compound characterized under 1., which comprises derivatizing the OH group located in the 3' and/or 2' position of the nucleoside, nucleotide or oligonucleotide to an amino or thiol group, and subsequently coupling on a fluorescent dye.

3. The use of the compounds characterized under 1. in
   a) the synthesis of complementary strands in the presence of a template strand,
   b) the synthesis of defined oligonucleotides,
   c) the detection thereof in vivo and in vitro,
   d) the detection of nucleic acids in vivo and in vitro and
   (e) the microscopic and macroscopic fluorescence detection in vivo and in vitro.

The invention is described in detail hereinafter, especially in its preferred embodiments. The invention is furthermore defined by the contents of the claims.

DESCRIPTION OF THE PREFERRED EMBODIMENTS

The compounds of the formula I are synthesized essentially by methods known from the literature (M. Gait, Oligonucleotide Synthesis, IRL-Press, Oxford 1984).

The coupling of the dye to the 3' and/or 2' position starts from a compound of the formula II, preferably from a nucleoside.

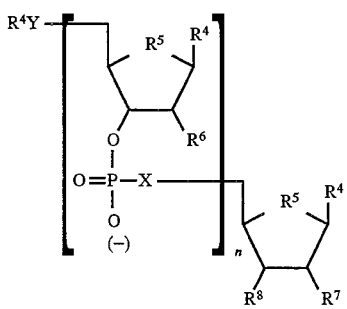

The compound of the formula II, in which $R^1$–$R^6$, X, Y and n have the abovementioned meanings, it being possible for the substituents to be identical or different and $R^7$ or $R^8$ being hydrogen, a hydroxyl or protected hydroxyl or methoxy group, is employed for the coupling. The coupling of the dye takes place via the hydroxyl group in the 3' and/or 2' position by introducing an amine or thiol.

A leaving group is introduced in the 3'-(2') position to introduce the azide. Suitable as leaving group is preferably triflate or mesylate or tosylate. The azide is introduced by a nucleophilic attack with azide, preferably lithium azide. The nucleophilic attack of a thiolate or S-protected thiolate yields the thiol or the protected thiol. The required stereochemistry at the sugar moiety of the nucleoside can best be achieved by $S_N2$ substitutions.

The amino group can be obtained straightforwardly via the azide and the subsequent reduction to the amine (Lit.: W. S. Mungall and R. L. Letsinger, J. Org. Chem., Vol. 40, No. 11, 1659 (1975)). The Staudinger reaction with triphenylphosphine and water is preferred in this step (Lit.: M. May and J. W. Engels, Nucl. Acids Res. 17, 15, 5973 (1989)).

The constitution and configuration of all the compounds were determined by NMR, elemental analysis, UV, IR etc.

After completion of the polycondensation it is possible to react the free 3'-(2')-amino or thiol group of the sugar moiety at the 3' end of the DNA with a reactive fluorescent dye by methods known from the literature (Hunkapiller, Nucl. Acids Res. 13, 2399, 1985; Hodges R. R. et al. Biochemistry, Vol. 28, 261 (1989)).

Alternatively, the amino group is also obtained by the Mitsunobu reaction (Synthesis, Vol 1, 1981, p. 1) and in accordance with the reaction described by Yamamoto et al. (J. Chem. Soc. Perk. Trans. 1, 1, 306, 1980).

The coupling of the fluorescent dye via the thiol group takes place in an analogous manner. However, in place of the azide a thiol group is introduced in protected or unprotected form.

The coupling of the fluorescent dye to the free amino group or thiol functionality of the nucleoside, nucleotide or oligonucleotide can, as an alternative, also take place only after use thereof. It is possible, for example, to carry out the fluorescent dye reaction after the termination step of the DNA or RNA sequencing reaction by labeling the entire mixture with the fluorescent dye.

It is possible in principle to use as fluorescent dyes all commercially available dyes which react with an amino or thiol group, preferably fluoresceins, rhodamines, Texas red, NBD (4-fluoro-7-nitrobenzofurazan from Sigma), coumarins, fluorescamines, succinylfluoresceins and dansyls.

The derivatized reaction mixture can be fractionated by a gel electrophoresis and detected by photometry or laser spectroscopy (H. Swerdlow and R. Gesterland, Nucl. Acids Res. 18, p. 1415 (1990)). Capillary electrophoresis (A. S. Cohen et al., P.N.A.S. US. 85, 9660 (1988)), for example packed with acrylamide gels, has also proven satisfactorily utilizable. In this case, detection preferably takes place at the outlet from the capillary (H. Swerdlow, S. Wu, H. Harke, N. Dovichi, Chromatography 516, 61 (1990)).

Starting from a compound of the formula I which has a triphosphate in the 5' position, it is possible to carry out the synthesis of the DNA double strand using any suitable primer and a template strand with the aid of a polymerase, i.e. an enzyme which in the presence of suitable substrates synthesizes a true complementary copy of the sequence, in the presence of the four nucleoside triphosphates, preferably with the aid of T7 or Taq polymerase, DNA polymerase I and reverse transcriptase. Suitable 5' protective groups are trityl, methoxy- or dimethoxytrityl (Gait, Oligonucleotide Synthesis, IRL Press, Oxford 1984).

The termination of the synthesis can be specifically determined in each case by using a 3'-(2')-amino-modified A,C, G,T nucleotide of the formula I. This is particularly important for the synthesis of DNA complementary strands in the presence of a template strand and thus also for the sequencing of DNA strands, because the use of a modified nucleotide ensures very base-specific termination of the reaction.

The synthesis of RNA nucleosides, nucleotides and oligonucleotides is carried out in an analogous manner.

It is furthermore possible to carry out the synthesis of derivatizable oligonucleotides with the aid of a starter nucleotide which has been amino- or thio-modified at the 3'-(2') end and immobilized on a polymeric support.

Suitable oligonucleotides are all DNA and RNA nucleotides prepared in a conventional way, but preferably with a length of 2 to 100, particularly preferably 12–50 nucleotides (chemical synthesis) or with a length of up to 3,000 nucleotides (enzymatic synthesis), depending on the efficiency of the polymerase used.

The oligonucleotide synthesis is carried out, starting from the starter nucleotide-support complex, in a conventional way, i.e. in the 3' and 5' direction and makes it possible to synthesize an oligonucleotide of defined sequence.

The immobilization of the starter nucleoside on commercially available supports takes place via a connecting arm (spacer) which can be cleaved after the synthesis; for example via the succinic acid linkage known from the literature or else via a linkage with urethane (Efimov et al., Nucl. Acids. Res. 11, 8369, 1983).

After the synthesis has taken place, the oligonucleotide must be cleaved off the support with suitable reagents. The derivatization with any suitable fluorescent dye takes place directly thereafter.

The oligonucleotides modified at the 3'-(2') end and synthesized in this way can then be used for the detection of, for example, complementary oligonucleotides.

The use according to the invention combines two advantages:

1) In the preparation of a labeled complementary strand there is simultaneous strand termination by the terminal 3'-(2')-amino- or thiol-modified nucleotide. The fluorescent dye labeling thereof at the 3'-(2') position additionally makes hazard-free detection possible.

2) In the preparation of exactly defined oligonucleotides the labeling of the starter nucleotide which is coupled to a support and is likewise 3'-(2')-amino- or thiol-modified makes possible accurate oligonucleotide synthesis combined with the possibility of fluorescence labeling and thus of detection.

The examples given below serve to illustrate the invention further.

EXAMPLES

1. Anomeric 3'- or 2'-amino- or azido-nucleoside 5'-triphosphates

Example 1

Synthesis of 5'-triphosphate-3'-amino-3'-deoxyriboside-thymidine

Scheme

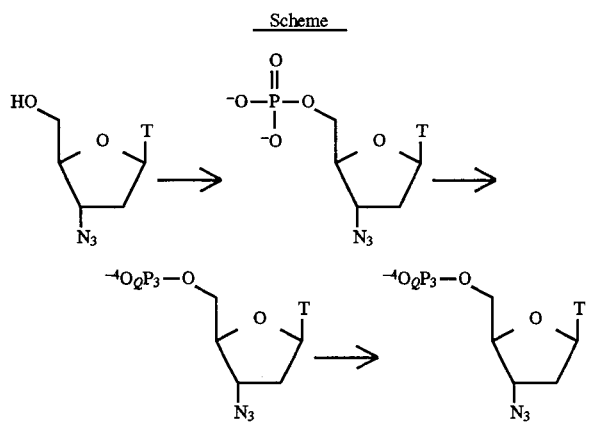

5'-Monophosphate-3'-azido-3'-deoxyriboside-thymidine

3'-Azidothymidine (Sigma) (160 mg, 0.6 mmol) is dissolved by stirring in 10 ml of triethyl phosphate. 0.2 ml of POCl$_3$ in 6 ml of triethyl phosphate is added from a dropping funnel to the solution at 4° C. After 24 h, the mixture is neutralized with 50 ml of saturated NaHCO$_3$ solution and extracted twice each with 60 ml of toluene and 100 ml of ether. The aqueous phase is diluted to 500 ml with distilled water and loaded onto an anion exchange column (®Sephadex A-25; 50×2.5 cm) which is loaded with HCO$_3^-$ as counter-ion by passing through 200 ml of 0.2M TBC buffer (triethylammonium bicarbonate buffer; pH 7.5 was set by itself). Purification is then carried out by passing through 300 ml of distilled water and elution is carried out first with 200 ml of 0.1M TBC buffer and then with a linear 0.1–0.2M TBC buffer gradient (total volume of gradient 1350 ml). One peak, the product peak, appears in the chromatogram. The product eluted at a buffer concentration of 0.12 to 0.15M TBC buffer. The TLC-positive 20 ml fractions are combined and concentrated by freeze drying. The triethylammonium bicarbonate is removed by adding ethanol several times. The product is in the form of a white crystalline triethylammonium salt.

Yield: 220 mg (56.2%); MW: 651.81; R$_f$ (ammonia:isoprop.:water 10:70:20): 0.40; 300 MHz-$^1$H-NMR (D$_2$O): 1.36 (t, 3H, CH$_3$); 1.90 (s, 3H, CH$_3$); 2.50 (m, 4H, 2',2"-H); 3.18–3.30 (dd, 2H, CH$_2$); 4.10 (m, 1H, 4'-H); 4.3 (m, 1H, 3'-H); 6.31 (t, 1H, 1'-H); 7.7 (s, 1H, 6-H); 11.50 (s, 1H, NH), 300 MHz-$^{31}$P-NMR (85% H$_3$PO$_4$ external, D$_2$O): 1.23 (s, 1P).

5'-Triphosphate-3'-azido-3'-deoxyriboside-thymidine

5'-Monophosphate-3'-azido-3',2'-deoxyriboside-thymine as triethylammonium salt (130 mg, 0.2 mmol) is dissolved in 6 ml of abs. DMF (dimethylformamide), and to the solution at 25° C. is added N,N'-carbonyldiimidazole (162.15 mg, 1 mmol) in 3 ml of abs. DMF while stirring. After a reaction time of 2 h, 1 ml of abs. methanol is added, the mixture is stirred for a further 15 min and the methanol is removed by distillation. The residue is mixed with 5 ml of a 0.2M solution of tri-n-butylammonium pyrophosphate in DMF and stirred at room temperature overnight. The precipitate composed of imidazole pyrophosphate is filtered off and washed with 20 ml of DMF, and the filtrate is concentrated in a rotary evaporator. The residue is dissolved in 250 ml of 0.1M TBC buffer, and the solution is loaded onto a Sephadex A-25 anion exchange column loaded with HCO$_3^-$. The product is purified by passing through 200 ml of distilled water and is eluted with a linear gradient from 0 to 0.5M TBC buffer (total volume of gradient 2,000 ml). Two peaks appear in the chromatogram, the first produced by the monophosphate and the second by the product. The product elutes at a buffer concentration of 0.30 to 0.35M TBC buffer. The positive 20 ml fractions are combined and concentrated by freeze drying. The triethylammonium bicarbonate is removed by adding ethanol several times. The product is in the form of a white crystalline triethylammonium salt.

Yield: 92 mg (50.4%); MW: 911.95; R$_f$ (ammonia:isoprop.:water 10:70:20): 0.14; 300 MHz-$^{31}$P-NMR (85% H$_3$PO$_4$ external, D$_2$O): −10.74 (d, $^2$J$_{PP}$=22.1 Hz, 1P, alpha-P atom); −11.45 (d, $^2$J$_{PP}$=21.9 Hz, 1P, gamma-P atom); −22.99 (t, $^3$J$_{PP}$=20.3 Hz, 1P, beta-P atom).

5'-Triphosphate-3'-amino-3'-deoxyriboside-thymidine

5'-Triphosphate-3'-azido-3',2'-deoxyriboside-thymine (68 mg, 0.075 mmol) is dissolved in 5 ml of dioxane/distilled water (2:1) and, while stirring at room temperature, triphenylphosphine (200 mg, 0.75 mmol) is added. The reaction mixture is stirred at 25° C. for 30 h and then the solvent is stripped off. The residue is dissolved in 30 ml of distilled water and extracted three times with 30 ml of ether each time. The aqueous phase is diluted to 150 ml and the solution is loaded onto a Sephadex A-25 anion exchange column loaded with HCO$_3^-$. The product is purified by passing through 200 ml of distilled water and is eluted with a linear gradient from 0 to 0.5M TBC buffer (gradient volume 2,000 ml). The chromatogram shows three peaks, the first representing the monophosphate compound 6, the second the product peak and the third the precursor peak 7. The product eluted at a buffer concentration of 0.40 to 0.42M TBC buffer. The positive 25 ml fractions are combined and concentrated by freeze drying. The triethylammonium bicarbonate is removed by adding ethanol. The product is in the form of an amorphous white triethylammonium salt.

Yield: 57 mg (85.7%); MW: 885.90; R$_f$ (ammonia:isoprop.:water 10:70:20): 0.08; 300 MHz-$^1$H-NMR (D$_2$O): 1.30 (t, 3H, CH$_3$); 1.92 (s, 3H, CH$_3$); 2.64 (m, 4H, 2',2"-H); 3.19–3.21 (dd, 2H, CH$_2$); 4.26 (m, 1H, 4"-H); 4.41 (m, 1H, 3'-H); 6.34 (t, $^3$J$_{HH}$=6.74 Hz, 1H, 1'-H); 7.69 (s, 1H, 6-H); 11.50 (s, 1H, NH). 300 MHz-$^{31}$P-NMR (85% H$_3$PO$_4$ external, D$_2$O); −10.75 (d, $^2$J$_{PP}$=22 Hz, 1P; alpha-P atom); −11.45 (d, $^2$J$_{PP}$=21.9 Hz, 1P, gamma-P atom); −22.05 (t, $^3$J$_{PP}$=20.4 Hz, 1P, beta-P atom).

Example 2

Synthesis of 1-(3'-amino-2',3'-dideoxy-5'-triphosphate-D-threopentofuranosyl)thymine Scheme

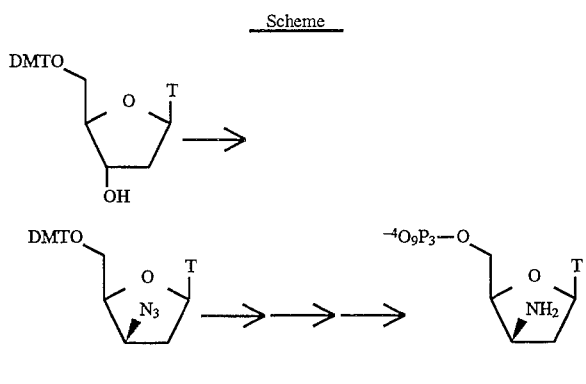

1-(3'-Azido-2',3'-dideoxy-5'-O-dimethoxytrityl-β-D-threopentofuranosyl)thymine

Carbon tetrabromide (11.91 mmol, 4.10 g) is added to a stirred solution of 5'-dimethoxytritylthymidine (for preparation, see M. Gait, Oligonucleotide Synthesis, IRL Press (1984), p. 27) (5.98 g, 11 mmol), triphenylphosphine (3.076 g, 11.73 mmol) and lithium azide (3.1 g, 55 mmol) in 37 ml of dry DMF. The mixture is stirred at room temperature (RT) for 56 h and then 15 ml of methanol are added. The product is subsequently precipitated in 800 ml of ice-cold distilled water. The precipitate is taken up in chloroform and purified by flash chromatography (ethyl acetate: n-hexane= 3:1). $R_f$ in chloroform:methanol 9:1=0.52. IR (cm$^{-1}$): 2100 azide, yield 80%, 4.95 g.

1-(3'-Amino-2',3'-dideoxy-5'-O-dimethoxytrityl-β-D-threopentofuranosyl)thymine

Triphenylphosphine (1.3 g, 4.94 mmol) is added to a stirred solution of 1-(3'-azido-2',3'-dideoxy-5'-O-dimethoxytrityl-β-D-threopentofuranosyl)thymine (0.5 g, 0.8 mmol) and left to react for 4 h. The phosphine imine is hydrolyzed by adding 3 ml of distilled water and stirring for a further 3 h. After the solvent has been removed in a rotary evaporator, the remaining oil is purified by flash chromatography (chloroform:methanol 99:1+1% triethylamine). $R_f$ in the same solvent=0.27.

The amine can be stained violet by treatment with ninhydrin on thin-layer chromatography (TLC). Yield 87.5%, 0.42 g. The product has the appropriate $^1$H-NMR spectrum.

Conversion to 1-(3'-amino-2',3'-dideoxy-5'-triphosphate-β-D-threopentofuranosyl)thymine For the subsequent conversion to the 5'-triphosphate, the dimethoxytrityl group is removed in analogy to the description of M. Gait, Oligonucleotide synthesis, IRL Press, p. 49 (1984), and the coupling of the triphosphate to the 5' position is carried out as mentioned in Example 1.

Example 3

Preparation of 2'-amino-2'-deoxy-5'-triphosphate-uridine

Scheme

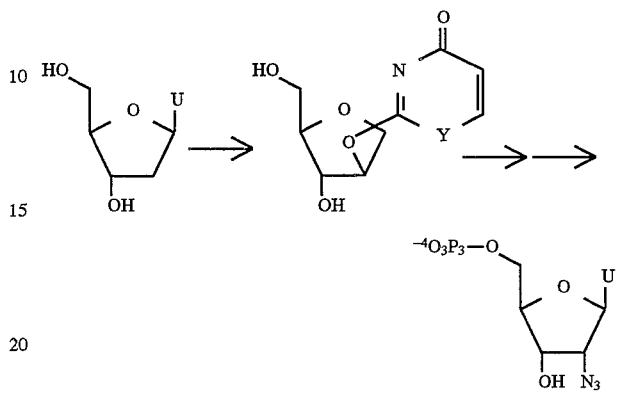

(2,2'-Anhydro-1-β-arabinofuranosyl)-uracil 0.5 g (5.93 mmol) of sodium bicarbonate was added to a solution of 19 g (77.8 mmol) of uridine and 22.2 g (103.6 mmol) of diphenyl carbonate in 75 ml of abs. dimethylformamide. After dissolution is complete, the clear colorless liquid is heated to a temperature of 150° C. for 30 min. After cooling, the cold solution is poured into absolute ether. The ether is decanted off from the resulting precipitate, and the crude product is recrystallized from 1650 ml of methanol. Drying results in a white crystalline powder.

Melting point: 239° C.; MS: 227; $R_f$: 0.31 methylene chloride/methanol 8:2; yield 9.22 g (52.3%). $^1$H-NMR 60 MHz corresponds to literature data.

2'-Azido-2'-deoxyuridine 1.16 g (10 mmol) of (2,2'-anhydro-1-β-arabinofuranosyl)-uracil and 3.5 g (71.7 mmol) of lithium azide are introduced with stirring into 25 ml of abs. DMPU (1,3-dimethyl-3,4,5,6-tetrahydro-2-(1-H)-pyrimidinol). The suspension is heated to 120° C., when the reaction solution becomes black. After 3 days, the black solution is diluted with 80 ml of water and extracted twice with 100 ml of methylene chloride. The combined organic phases are then washed four more times with water and are concentrated in a rotary evaporator. The solid tarry residue is purified by column chromatography on silica gel (methylene chloride/methanol 8:2). After the black oily residue has been concentrated on a rotary evaporator, it is purified twice more on a silica gel basis (acetone: methanol 8:3 and acetone:ethyl acetate 1:1). A colorless glass which is pure in the TLC ($R_f$ methylene chloride/methanol 8:1=0.61) is obtained. Yield 2.035 g (30%). IR (chloroform film): 2120 cm$^{-1}$. MS(FAB): 270. The product has the expected $^1$H-NMR spectrum.

2'-Amino-2'-deoxy-5'-triphosphate-uridine is prepared by selective 3'-acylation of the hydroxyl functionality. The introduction of the 5'-triphosphate group is subsequently carried out in analogy to Example 1. After deacylation at the 3' position, the azide is reduced to the amine by reaction with triphenylphosphine (as in Example 2).

Example 4

Synthesis of 3'-amino-2',3'-dideoxy-5'-triphosphate-adenosine

Scheme

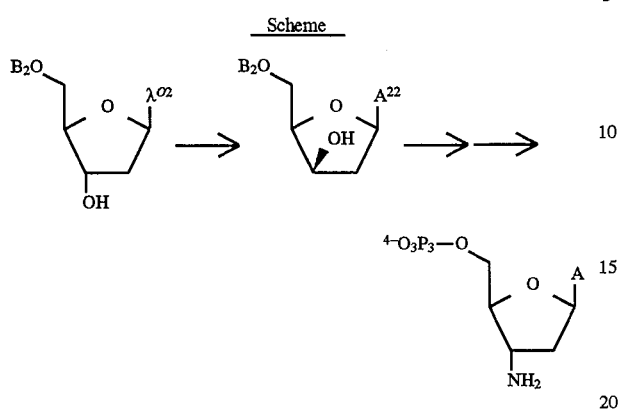

N⁶-Benzoyl-9-(5-O-benzoyl-2-deoxy-β-D-threo-pentofuranosyl)adenine

A suspension of 920 mg (2 mmol) of $N^6,5'$-O-dibenzoyl-2'-deoxyadenosine (was prepared by the method described by Nishino et al., Nucleosides & Nucleotides 1986, 5, 159) in 30 ml of abs. dichloromethane (contains 2 ml of pyridine) is cooled to −30° C., and 5 ml of a solution of trifluoromethanesulfonic anhydride in dichloromethane (10% by vol.) are slowly added dropwise. After removal of the cooling bath, the solution is left to warm and 1 ml of water is added. After 3 h, a further 5 ml of water are added and the organic phase is washed. After removal of the solvent, the remaining residue is dissolved in 50 ml of methanol, and 100 mg of sodium bicarbonate are added. The mixture is stirred for a further 2 h at RT, neutralized with 10% strength acetic acid, the solvent is removed by distillation, and purification is carried out by flash chromatography on silica gel (chloroform:methanol 97:3). Yield 710 mg (1.48 mmol) 75%. $R_f$ chloroform:methanol 97:3=0.49. MS=459.

3'-Azido-2',3'-dideoxyadenosine

A solution of 920 mg (2 mmol) of N⁶-benzoyl-9-(5-O-benzoyl-2-deoxy-β-D-threopentofuranosyl)-adenine in 20 ml of abs. dichloromethane (and 2 ml of pyridine) is cooled to −30° C. Then 5 ml (3 mmol) of a solution of trifluoromethanesulfonic anhydride in abs. dichloromethane are added dropwise. The cooling bath is removed, the mixture is stirred for a further 20 min, and 980 mg (20 mmol) of lithium azide in 20 ml of DMF are added to the solution. After stirring at RT for a further 2 h, 50 ml of water and 150 ml of chloroform are added, and the organic phase is taken up and washed with distilled water. The solvent is removed in a ®Rotavapor and the product is treated with ammoniacal methanol solution overnight to remove the base protective group. Renewed removal of solvent is followed by purification by flash chromatography (chloroform:methanol 95:5) on silica gel. Yields 430 mg (1.6 mmol, 79%) of white crystalline powder. IR: 2,100 cm⁻¹ azido group.

3'-Amino-2',3'-dideoxy-5'-triphosphate-adenosine

The 5'-triphosphate is prepared in analogy to Example 1. The azide is subsequently reduced to the amine as in Example 2.

Example 5

Synthesis of 3'-amino-2',3'-dideoxy-5'-triphosphate-guanosine

Scheme

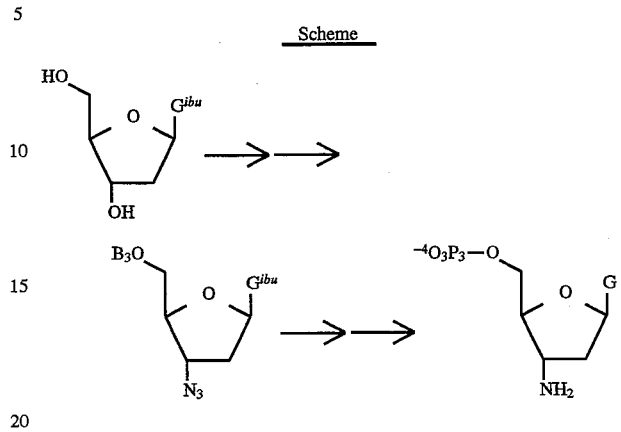

3'-Amino-2',3'-dideoxy-5'-triphosphate-guanosine is prepared starting from $N^2$-isobutyryl-5'-O-benzoyl-2'-deoxyguanosine which can be prepared by the method of Nishino et al. (Nucleosides & Nucleotides 5, 159, 1986). The nucleoside is converted into the 3'-azide in analogy to the preparation in Example 4. It should be noted in this case that no treatment with ammoniacal methanol solution is carried out because the removal of the isobutyryl protective group takes place only after introduction of the triphosphate group and before the reduction of the azide to the amine. The method mentioned in Example 1 is used for the conversion to the triphosphate in the case of guanosine too. The reduction to the amine is described in Example 2.

2. Synthesis of 3'-amino oligomers and subsequent 3'-fluorescence labeling

Example 6

The Synthesis of an oligomer of 20 nucleotides 3'-H₂N-TTTTTTTTTTTTTTTTTTTT-5' starts from 5'-dimethoxytrityl-protected 3'-amino-3'-deoxythymidine. This compound is prepared as described in Example 1. In this case the starting material is 5'-dimethoxytrityl-protected AZT (azido-3'-deoxyriboside-thymidine) which can be prepared from AZT and dimethoxytrityl chloride by the method of M. Gait (oligonucleotide Synthesis, IRL Press 1984, p. 27).

The compound is subsequently reduced as described in Example 1 with triphenylphosphine. The next stage is the preparation of the support material. For this 200 mg of 5'-O-(4,4'-dimethoxytrityl)-3'-amino-3'-deoxythymidine are introduced into 700 μl of abs. pyridine. To this solution are added 45 mg of DMAP (dimethylaminopyridine) and subsequently 40 mg of succinic anhydride. The mixture is left to stand overnight and then remaining succinic anhydride is hydrolyzed by adding 10 μl of water. Co-evaporation with toluene is carried out three times, and the residue is taken up in 12 ml of methylene chloride, washed with 4 ml of cold citric acid (10% strength) and twice with 4 ml of water. The organic phase is dried over sodium sulfate, the solvent volume is concentrated, and the substance is dissolved in 1 ml of methylene chloride. This solution is slowly added dropwise with stirring to 30 ml of n-hexane. The precipitate which has separated out is filtered off with suction and dried at 40° C. under oil pump vacuum. The further preparation of the CPG-based support material is carried out by standard protocols and the standard cycle (ABI 380A User Bulletin, Issue No. 36, July 1986) on an ABI 380 A DNA synthesizer by the phosphoramidite process is subsequently used to prepare the oligomer of 12 nucleotides. After deprotection and cleavage of the 3'-aminooligonucleotide of the support, purification and characterization are by standard methods. In this case, better results can be achieved by using more base-labile coupling methods for attachment to the support. It is beneficial to replace the acid amide which is to be cleaved by a urethane functionality as described by Efimov (Nucleic Acid Res. 11, 8369, 1983).

Example 7

The synthesis of an oligomer of 23 nucleotides with 3'-amino end 3'-H₂N-ACACCCAATTCTGAAAATGGAT-5' is carried out as described in Example 1. Purification and characterization are by standard methods.

Example 8

The subsequent derivatization of the oligomers at the 3'-amino terminus is carried out with fluorescein isothiocyanate. 50 nmol of the 3'-aminooligonucleotide are dissolved in 25 μl of a 500 mM sodium bicarbonate solution in an Eppendorf tube. 20 μl of a 300 mM FITC solution (Sigma) in DMSO are added. After a reaction time of 6 h at room temperature, the reaction mixture is purified by passing in a 20 mM ammonium acetate solution through a Sephadex G-25 column. The 3'-FITC oligomer was analyzed by an analytical HPLC run both by fluorescence detection and by UV detection. The HPLC results were also verified by analyses on a capillary gel electrophoresis (supplied by Dionex).

Formula of fluorescein isothiocyanate:

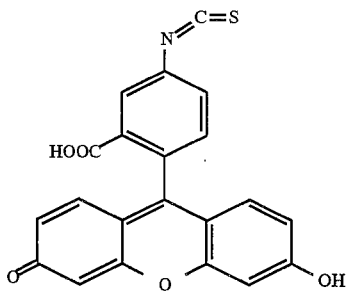

Example 9

Both 3'-aminooligomers from Example 1 and 2 are reacted by the method as described in Example 3 with rhodamine isothiocyanate and tetramethylrhodamine isothiocyanate. The 3'-fluorescence-labeled oligomers are analyzed by an analytical HPLC run both by fluorescence detection and by UV detection. The HPLC results were also verified by analyses on a capillary gel electrophoresis (supplied by Dionex).

Formulae of the dyes rhodamine isothiocyanate and tetramethylrhodamine isothiocyanate

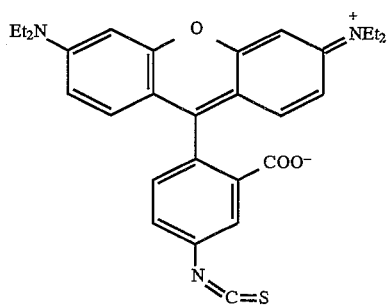

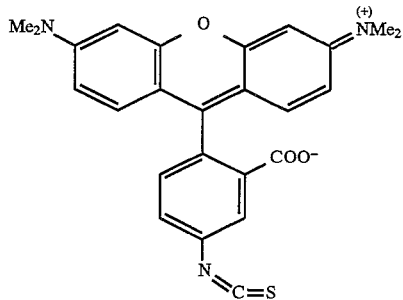

Example 10

Both 3'-aminooligomers from Example 1 and 2 are reacted by the method as described in Example 3 with the depicted coumarin derivative. The 3'-fluorescence-labeled oligomer is analyzed by an analytical HPLC run both by fluorescence detection and by UV detection. The HPLC results are also verified by analyses on a capillary gel electrophoresis (supplied by Dionex).

Formula of the coumarin dye molecule:

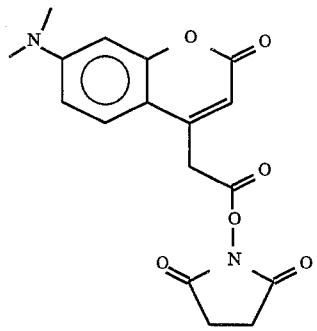

3. Incorporation of Modified Nucleotides by DNA Polymerases and Analysis of the Sequencing Experiments To check the acceptance of the amino triphosphates by the conventional sequencing enzymes, appropriate termination solutions were prepared and the polymerases (Klenow, Boehringer; Taq, Amersham; T7, Pharmacia; Sequenase, USB) were tested. This entailed analysis of the incorporation rates and the termination properties of the triphosphates both classically and by the labeling with fluorescent dyes.

Example 11

The 5'-triphosphate-3'-amino-3'-deoxyriboside-thymidine prepared as in Example 1 was replaced by 2',3'-dideoxy-5'-triphosphate-thymidine. This was carried out with the termination solutions of all the polymerases indicated above. In each case, equimolar, ten times higher and ten times lower dNTP/terminator ratios were tested. The sequencings were carried out by standard protocols. Autoradiographic detection in these investigations was by the incorporation of alpha-[35]S-dATP. It emerged that a) the 3'-amino-nucleotide has a terminating action on the enzymes used, b) the incorporation rates in the case of T7, Taq and Sequenase are identical to the customary dideoxy terminators and c) finally sequencing is possible without problems using the amino-nucleotide.

Example 12

The compound 5'-triphosphate-3'-amino-3'-deoxyriboside-thymidine was reacted with fluorescein isothiocyanate to give 5'-triphosphate-3'-amino-3'-deoxyriboside-3'-N-fluorescein isothiocyanate-thymidine.

5'-Triphosphate-3'-amino-3',2'-deoxyriboside-thymine (2.5 mg, 2.8 μmol) is dissolved in 200 μl of distilled water in an Eppendorf cap, and 200 μl of 1M $Na_2CO_3$/$NaHCO_3$ buffer (pH 9) are added. The reaction mixture is protected from daylight by wrapping in aluminum foil, and 80 μl of a fluorescein isothiocyanate solution (10 mg in 1 ml of DMF) are added with a 100 μl pipette. After a reaction time of 10 min at room temperature there is quantitative conversion of the precursor in the TLC. Purification is by gel filtration. The Sephadex G-10 column is protected from light by wrapping in aluminum foil, subsequently the complete reaction mixture is loaded onto the column material and eluted with water at a flow rate of 1 ml/min. The chromatogram shows two peaks. The first peak is produced by the product and the second by unreacted dye. The size of the fractions is 5 ml, a total of 24 fractions being obtained. Based on the chromatogram, fraction 4 proves to be positive. This is confirmed by TLC. The solvent is removed by lyophilization, and the substance is stored at −80° C. Yield 3.32 mg (93%); MW: 1,274.32; $R_f$ (ammonia:isopropanol:water 10:70:60)=0.62; fluorescence emission spectrum: the wavelength of the incident light is 420 nm. The emission maximum of the compound is at 514.8 nm. A 2.5 mM solution in distilled water was measured. The emission maximum of a 2.5 mM solution of the underivatized dye in distilled water is at a wavelength of 519.4 nm.

The prepared 5'-triphosphate-3'-amino-3'-deoxyriboside-3'-N-fluorescein-isothiocyanate-thymidine was replaced by 2',3'-dideoxy-5'-triphosphate-thymidine. This was carried out with the termination solutions of all the polymerases indicated above. In each case equimolar, ten times higher and ten times lower dNTP/terminator ratios were tested. The sequencings were carried out by standard protocols. Autoradiographic detection in these investigations was by the incorporation of alpha-[35]S-dATP. It emerges that a) the 3'-fluorescence-labeled nucleotide has a terminating action on the enzymes used, b) the incorporation rates in the case of T7, Taq and Sequenase are, because of the sterically demanding dye residue, identical at ten times higher concentrations to the conventional dideoxy terminators, and c) sequencing is possible without difficulty using the 3'-fluorescence-labeled terminator.

Example 13

The prepared 5'-triphosphate-3'-amino-3'-deoxyriboside-3'-N-fluorescein-isothiocyanate-thymidine was replaced by 2',3'-dideoxy-5'-triphosphate-thymidine. This was carried out with the termination solutions of T7 and Taq polymerases. Ten times higher dNTP/terminator ratios were used as a basis. The sequencings were carried out by standard protocols. No incorporation of alpha-[35]S-dATP was carried out in these investigations, and the sequence analysis was carried out successfully with the 3'-fluorescence-labeled terminator in a commercially available DNA sequencer.

Example 14

5'-triphosphate-3'-thio-3'-deoxyriboside-thymidine

Scheme:

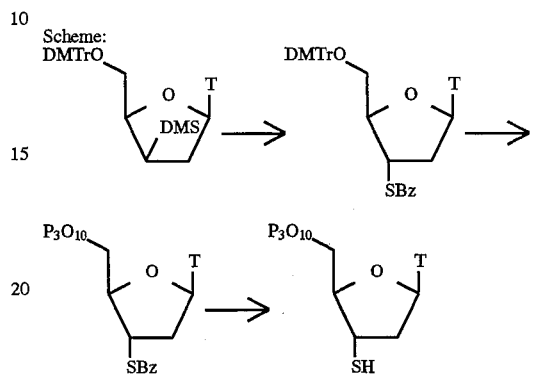

5'-O-Dimethoxytrityl-3'-S-benzoyl-thiothymidine

The introduction of sulfur at the 3' position is carried out by replacing a leaving group (mesylate) with sodium thiobenzoate.

The sodium thiobenzoate is synthesized by adding 10M NaOH to an ice-cold solution of thiobenzoic acid (10 g) in water 15 ml until the solution is just alkaline. The pH is subsequently adjusted to pH 7 with aqueous thiobenzoic acid, and the solution is cooled to −5° C. and filtered to remove solid residues. After removing the water in a rotary evaporator with ethanol, the yellow salt is dried over phosphorus pentoxide in vacuo. A solution of 5'-O-dimethoxytrityl-3'-O-methanesulfonyl-2'-deoxyxylothymidine (8.45 mmol) (synthesis of the mesylate: Miller, Fox (1964) J. Org. Chem. 29, 1772) and sodium thiobenzoate (33 mmol) in DMF (30 ml) is stirred at 100° C. for 4 h. The mixture is extracted with dichloromethane and the org. phase is washed with saturated $NaHCO_3$ solution and saturated NaCl solution. Drying of the organic phase over sodium sulfate is followed by coevaporation with toluene twice and purification of the oily crude product by flash chromatography (silica gel 60H, chloroform/methanol 0–10%).

Yield: 60%, the product has the expected $^1$H-NMR spectrum.

The 5'-dimethoxytrityl protective group is cleaved off for the phosphitylation at the 5' position by methods known from the literature (M. Gait, Oligonucleotide Synthesis, IRL Press, Oxford 1984). The 5'-triphosphate is subsequently prepared by the method of Eckstein and Ludwig (J. Org. Chem., 1989, Vol. 54, No. 3, 631) with salicyl phosphochloridite (Aldrich) and treatment with pyrophosphate. The thiol is liberated by reaction with 10M NaOH in argon-saturated ethanol (R. Cosstick, Nucleic Acids Research 18, 4, 829). The 3'-thio-5'-triphosphate-thymidine was coupled by the method in Example 8 with iodoacetamidofluorescein (Molecular Probes), and an 80% yield of the fluorescence-labeled thionucleotide is obtained in this step.

Example 15

Synthesis of 1-(3'-thio-2'-,3'-dideoxy-5'-triphosphate-β-D-threopentofuranosyl)thymine Scheme:

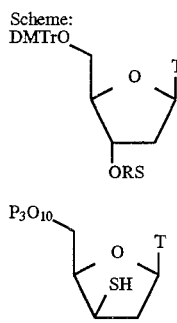

Replacement with sodium thiobenzoate is carried out as described in Example 14 starting from 5'-DMTr-O-, 3'-O-mesyl-thymidine. This is followed by the 5' protective group being cleaved off, the 5'-triphosphate being introduced, the thiol being liberated and the attachment of iodoacetamidofluorescein being carried out in analogy to the procedures in Example 14.

Example 16

Synthesis of an Oligomer of 10 Nucleotides 3'-β-H$_2$N-TTT TTT TTT T-5'

The synthesis of an oligomer 3'-β-H$_2$N-TTT TTT TTT T-5' starts from 1-(3'-amino-2'-,3'-dideoxy-5'-DMTr-β-D-threopentofuranosyl)-thymine which is reacted by the method as described in Example 6 to give the support material for the phosphoramidite method. The subsequent fluorescence labeling of the 3'-β-amino-oligonucleotide with fluorescein isothiocyanate is carried out as in Example 8.

We claim:

1. A method for the synthesis of labeled 3'-amino- and thiol-modified DNA and RNA oligonucleotide strands which comprises synthesizing the strand using a suitable primer, a template strand and a polymerase in the presence of four nucleoside triphosphates, and terminating the synthesis with a 3'-(2')amino-modified nucleotide compound of the formula I

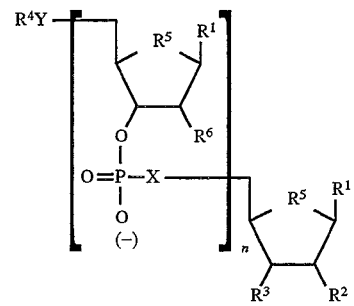

in which

R$^1$ is a purine or pyrimidine base, wherein R$^1$ can in each case be identical or different, R$^2$ is hydrogen, a hydroxyl, a protected hydroxyl or methoxy group in α- or β-position, R$^3$ is a fluorescent dye in the α or β-position bonded via an amino or thiol group, n is a number greater than or equal to zero and less than 3000, R$^4$ is a 5' protective group or phosphate, pyrophosphate or triphosphate, R$^5$ is oxygen, R$^6$ is a hydroxyl, methoxy group or hydrogen in α- or β-position, where R$^6$ can in each case be identical or different, and X and Y are oxygen or sulfur, where X and Y can in each case be identical or different in the synthesis.

2. A method for microscopic and macroscopic fluorescence detection in vivo and in vitro of labeled oligonucleotides synthesized according to the method of claim 1.

3. The method according to claim 1, wherein said synthesis of labeled DNA and RNA oligonucleotides is carried out in the presence of the complement of said DNA and RNA oligonucleotides.

* * * * *